United States Patent
Leinenbach et al.

(10) Patent No.: US 10,780,211 B2
(45) Date of Patent: Sep. 22, 2020

(54) APPARATUS FOR CARRYING OUT AN APHERESIS TREATMENT

(71) Applicant: FRESENIUS MEDICAL CARE DEUTSCHLAND GMBH, Bad Homburg (DE)

(72) Inventors: Hans-Peter Leinenbach, Krems (AT); Frank Gebauer, Mautern (DE); Gerhard Mager, Bad Homburg (DE); Juergen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 442 days.

(21) Appl. No.: 15/552,106

(22) PCT Filed: Feb. 16, 2016

(86) PCT No.: PCT/EP2016/000262
§ 371 (c)(1),
(2) Date: Aug. 18, 2017

(87) PCT Pub. No.: WO2016/131539
PCT Pub. Date: Aug. 25, 2016

(65) Prior Publication Data
US 2018/0043082 A1    Feb. 15, 2018

(30) Foreign Application Priority Data
Feb. 18, 2015   (DE) .................. 10 2015 002 073

(51) Int. Cl.
*A61M 1/34*    (2006.01)
*A61M 1/36*    (2006.01)
(Continued)

(52) U.S. Cl.
CPC ........ *A61M 1/3486* (2014.02); *A61M 1/3496* (2013.01); *A61M 1/367* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 5,637,082 A | 6/1997 | Pages et al. | |
| 2002/0110485 A1* | 8/2002 | Stringer | A61M 1/3626 422/45 |

FOREIGN PATENT DOCUMENTS

| | | |
|---|---|---|
| DE | 4338858 | 4/1995 |
| DE | 19729591 | 2/1999 |

(Continued)

OTHER PUBLICATIONS

Machine translation of DE 43 38 858 from EPO. (Year: 1995).*

*Primary Examiner* — Leslie R Deak
(74) *Attorney, Agent, or Firm* — Jacobson Holman, PLLC.

(57) ABSTRACT

The present invention relates to an apparatus for carrying out an apheresis treatment, wherein the apparatus has an extracorporeal circuit in which a regenerable single adsorber is located for separating substances from blood or for separating substances from plasma acquired by means of a plasma separator, wherein a line is provided for conducting the blood or the plasma which extends to the adsorber and via which blood or plasma is applied to the adsorber, wherein a reservoir is provided for receiving blood or plasma and is arranged upstream of the adsorber in the line or is in communication with the line upstream of the adsorber; and in that a controller or switching means is provided which is configured such that the reservoir is filled with blood or
(Continued)

Figure 1:
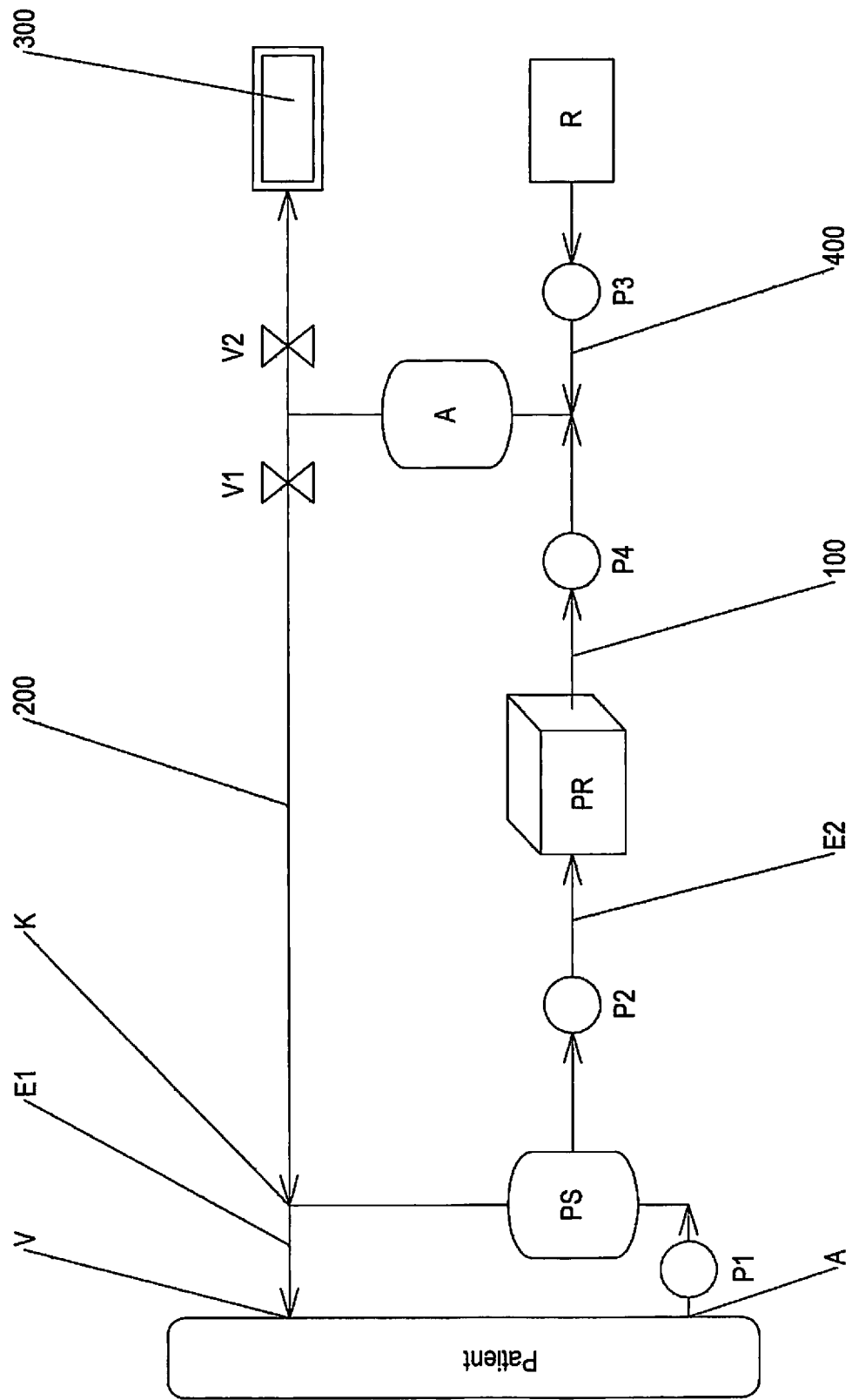

plasma and the application of blood or plasma to the adsorber is suppressed when the regeneration of the adsorber is carried out.

12 Claims, 8 Drawing Sheets

(51) Int. Cl.
*A61M 1/02* (2006.01)
*A61M 1/38* (2006.01)
(52) U.S. Cl.
CPC ......... *A61M 1/3679* (2013.01); *A61M 1/0209* (2013.01); *A61M 1/38* (2013.01)

(56) References Cited

FOREIGN PATENT DOCUMENTS

| | | |
|---|---|---|
| DE | 10157569 | 6/2003 |
| DE | 69733853 | 5/2006 |
| EP | 0111696 | 6/1984 |
| EP | 0263384 | 4/1988 |
| EP | 0414006 | 2/1991 |
| WO | WO 87/07531 | 12/1987 |

\* cited by examiner

APPARATUS FOR CARRYING OUT AN APHERESIS TREATMENT

The present invention relates to an apparatus for carrying out an apheresis treatment, wherein the apparatus has an extracorporeal circuit in which a regenerable single adsorber is located for separating substances from blood or for separating substances from plasma acquired by means of a plasma separator, wherein a line is provided for conducting the blood or the plasma which extends to the adsorber and via which the adsorber is acted on by blood or plasma.

Adsorbers known from the prior art are medical products which serve the depletion of blood plasma components. They typically comprise a matrix which is located in a housing which can be flowed through. A retention system ensures that the matrix, which can e.g. be configured as a particulate matrix, remains in the housing. The adsorber matrix typically has a surface which is especially modified to be able to bind the desired target molecule(s) from the blood plasma and thus to be able to remove them from the plasma.

In immune apheresis, regenerable adsorbers for reuse are currently used and also disposable-adsorbers are used which are only used once and then discarded. The disposable adsorbers are not regenerated and are thus limited with respect to their bonding capacity. This limitation is in particular undesired with target molecules to be removed which are present at high concentrations in the blood plasma which is also simply called plasma within the framework of the invention. Regenerable adsorbers are known to remedy this. On their use, the processing of the plasma is interrupted and the adsorber is regenerated before the processing of the plasma is continued.

In order not to have to accept any interruption of the treatment, the so-called dual column process is used in which the two adsorber columns are charged and regenerated alternately. A continuous processing of the plasma can thus take place and the desired depletion of the target molecule can be achieved via the number of regeneration cycles.

Regenerable adsorbers typically require a separation of the blood plasma from the full blood. This separation takes place in parallel with the immunoapheretic plasma processing in a second connected extracorporeal circuit, wherein the processed plasma is continuously reinfused into the patient again together with the fraction of the blood containing the blood cells.

Conventional regenerable adsorbers of dual column systems are reused several times with the same patient due to their high costs, which requires an intermediate preservation. The preservation solution(s) contain(s) ingredients such as inter alia mercury in thiomersal from which a potential risk for the patient arises when the flushing free of the adsorber prior to use is not carried out sufficiently or is not carried out at all. The filling of the adsorber with the preservation solution and the flushing free prior to the next use represent an additional workload for the user. Apart from this, the preservation solution represents environmental pollution.

Apart from these disadvantages, the regulation of the blood flow and of the plasma flow as well as the regulation of the flow of the different solutions is also comparatively complex and/or expensive. The complex control makes high demands on the managing of the risks which are associated with the complex therapy process.

Single column therapy processes provide a plurality of advantages in comparison. The treatment system is less complex with respect to dual column processes and can thus be integrated more easily into acute treatment machines. An additional monitor for processing the columns is not necessary and the process becomes more secure because no parallel processing of plasma and toxic solutions such as the elution solution takes place.

It is a disadvantage of the single column therapy process that no treatment can take place, i.e. no adsorption of pollutants at the adsorber, during the regeneration of the column or of the adsorber. The total treatment time is thus extended by the duration of the regeneration phases. There is not therapeutic benefit during these phases. The interruption of the therapy during the regeneration phases represents a reduction in the availability of the apparatus, which may have the consequence that therapy-relevant substances cannot be removed from the blood of the treated patient at the required rate. With acute courses of disease, this means a treatment delay and thus a delay in the improvement of the patient's state by the TA therapy (TA=therapeutic apheresis). There is a substantial comfort disadvantage for mobile patients.

It is the underlying object of the present invention to further develop an apparatus of the initially named kind such that time losses and availability restrictions in single column or simple treatment processes are minimized and, in the ideal case, the time requirement of regenerations of the adsorber is eliminated from a therapeutic viewpoint.

This object is achieved by an apparatus having the features described below. Provision is accordingly made that the apheresis apparatus has at least one reservoir for receiving blood or plasma which is arranged upstream of the adsorber in the line or is in communication with the line upstream of the adsorber and that at least one controller or switching means is provided which is configured such that the reservoir is filled with blood or plasma in at least one switching state of the controller or switching means and the application of blood or plasma to the adsorber is suppressed when the regeneration phase of the adsorber is initiated.

In the case of the use of a controller, the apparatus works automatically, i.e. it is instigated by the controller to fill the reservoir and the application on the adsorber is suppressed when it is signaled to the controlled that the regeneration phase of the adsorber is being initiated. Such a signaling can take place downstream of the adsorber after the end of a specific treatment phase, i.e. after the end of a specific treatment duration of the adsorber, or in dependence on other parameters such as in dependence on the measured concentration of the substances to be adsorbed.

However, the case is also covered by the invention that a switching means is present which is to be actuated by a user. If it is found that the regeneration of the adsorber is being initiated, the user actuates the switching means, which has the result that e.g. pumps, valves or the like are operated such that the filling of the reservoir and the application of blood or plasma to the adsorber is suppressed for the duration of the regeneration.

The controller or the switching means are in communication with means, in particular with one or more pumps and/or valves, for controlling the blood flow or the plasma flow such that the desired filling of the reservoir with blood or plasma and the blocking of the adsorber with respect to the application of blood or plasma to it takes place.

Provision is made in accordance with the invention that on the regeneration of the adsorber with a regeneration fluid, the blood flow or the plasma separation is not interrupted, but is rather continued at least at times, with the blood or the plasma being collected in a reservoir until the regeneration is completed and the treatment, i.e. the adsorption in the adsorber, can be continued.

The basic idea is thus the continuation of the plasma generation or of the blood conveying during the regeneration phase of the adsorber which is configured as a single column adsorber or as any other simple adsorber. An adsorber is to be understood by this which, unlike dual column systems, is used as a single adsorber. The continuation of the plasma generation or of the blood conveying can extend over the total duration of the regeneration phase of the adsorber or over a part of the regeneration duration, for example until the reservoir is completely full.

The blood or the acquired plasma is buffered in the reservoir. In the subsequent treatment phase, in addition to the blood which is still continuously conveyed or to the plasma which is still continuously acquired, the blood or plasma stored in the reservoir is conducted over the adsorber at a correspondingly higher flow rate.

In the case of the treatment of blood plasma, the reservoir is arranged downstream of the plasma source, i.e. generally between the plasma pump and the adsorber. In the case of the treatment of full blood, the reservoir is arranged between the arterial inlet of the patient and the adsorber.

The speed-determining step of the TA process is the plasma generation rate. The patient inlet, i.e. the available blood flow and the plasma portion which can be reliably separated without interfering with the process is decisive. Plasma flow rates of 15-25 ml/min are typically achieved in plasma generation by hemofiltration.

The present invention covers any desired type of plasma separation such as the use of a plasma filter, of a centrifuge, etc.

To be able to process the comparatively high volume flow on the emptying of the reservoir, the adsorber must be able also to work properly at much higher flows. The binding processes at the adsorber must be sufficiently fast, i.e. the binding between the adsorber and the substance in the blood or in the plasma must have a sufficiently high binding constant. In addition, the flow properties such as the flow profile, the flow resistance and thus the resulting pressure drop over the length of the adsorber may not deteriorate appreciably over the length of the adsorber at a higher flow rate. In individual cases, the plasma flow over the adsorber has to be limited to a maximum value.

The adsorber is preferably arranged in a line section of the extracorporeal circuit in which blood plasma is present, i.e. the adsorber has blood plasma applied to it. Provision is accordingly made in an preferred embodiment of the invention that a first extracorporeal circuit is provided in which the plasma separator is located whose secondary side is adjoined by a second extracorporeal circuit, wherein the reservoir and the adsorber are arranged in the second extracorporeal circuit, and wherein a return line is provided which connects the adsorber to the first extracorporeal circuit. The first extracorporeal circuit is in communication with the patient via an arterial inlet and via a venous inlet and contains a plasma separator, e.g. in the form of a plasma filter. On the secondary side, i.e. on the side of the acquired plasma, a second extracorporeal circuit is located in which the reservoir is located and, downstream thereof, the adsorber.

The present invention is, however, not restricted to this and also covers systems which have an adsorber to which full blood is applied.

In a preferred embodiment of the invention, the reservoir is located between the plasma pump or between the first plasma pump (this means the first pump in the plasma branch after the plasma separation from the full blood) and the adsorber.

The linking of the reservoir to the flow path of the blood or of the plasma can take place in different manners: it is conceivable that the reservoir is flowed through by blood or plasma and thus has at least one in-line and at least one out-line.

Alternatively, the reservoir can be arranged as a secondary branch or in a secondary branch of the line conducting the blood or the plasma.

Alternatively, the reservoir can be arranged in a line section in parallel with the line conducting the blood or the plasma.

The controller or the switching means can be configured such that it suspends the plasma separation or the conveying of the full blood when the maximum volume in the reservoir is reached and the regeneration cycle has not yet ended.

It is also conceivable that the controller or the switching means is configured such that it first initiates the conveying of the total separated plasma into the reservoir and switches over to a bypass about the adsorber when the maximum volume in the reservoir is reached and the regeneration cycle has not yet ended. The bypass is configured such that it bypasses the adsorber and returns the generated plasma via the return line to the first extracorporeal circuit and thus to the patient again.

It is also conceivable that the controller or the switching means is configured such that a portion of the separated plasma into the reservoir and simultaneously a partial plasma return is carried out. If the maximum volume in the reservoir is reached and if the regeneration cycle has not yet ended, a complete return of the separated plasma takes place.

Means can be provided, preferably in the form of pumps and/or valves, for emptying the reservoir, wherein the controller or the switching means is in communication with the means for emptying the reservoir and activates them when the regeneration phase of the adsorber has ended. The emptying of the reservoir can thus be initiated automatically, i.e. instigated by a controller or by the switching means, i.e. instigated by a user.

The means for filling the reservoir can be formed by a pump arranged downstream of the plasma separator, by the blood pump, by a pump which is arranged in a line leading to the reservoir or by a pneumatic actuator.

If the fluid which is applied to the adsorber is plasma, i.e. blood plasma, the plasma pump which directly follows the plasma separator, i.e. which is arranged directly downstream of the plasma separator, preferably serves as the means for filling the reservoir. This is necessary independently of whether a reservoir is present. It serves for generating a defined plasma flow from the plasma separator.

In principle, the filling of the reservoir can also take place by another pump, e.g. by a pump arranged in a side branch of the blood flow path or of the plasma flow path.

A pneumatic filling of the reservoir is also conceivable. On the use of a rigid hollow body, a pneumatic actuator unit can thus be connected by which a vacuum is generated in the hollow body. It can be connected to the ventilation of the hollow body. The pump function can also take place pneumatically with flexible or elastic hollow bodies if they are placed in a mount which is arranged at the device side, which is rigid and which can be sealed with respect to environmental air.

The vacuum generation in the hollow body can also take place by external mechanical forces such as by a syringe or by a pair of bellows mechanically mounted at both sides.

Provision can furthermore be made that the means for emptying the reservoir are formed by gravity, by a pump arranged downstream of the reservoir, by a pump which is arranged in a line leading off from the reservoir, by a pneumatic actuator or by the elastic material of the reservoir.

It is pointed out at this point that the terms "upstream" and "downstream" characterize the arrangement with respect to the flow direction of the blood or of the plasma during the treatment or during the filling and emptying of the reservoir.

In the simplest case, the emptying takes place by gravity in that the reservoir is arranged at a sufficient height above the adsorber. The flow resistance of the adsorber and the venous return pressure have to be applied by gravity. Alternatively or additionally to the use of gravity, an elastic hollow body can be used which sets the plasma or the blood under a pre-pressure by stretching its walls. There is the advantage with this arrangement of a comparatively simple arrangement; however there is the disadvantage that the flow cannot be controlled actively or only with limitations.

In principle, means for the measurement of the volume, of the level or of the flow can be used as a regulable alternative or addition to the described pneumatically operated arrangements.

A controlled emptying is possible by means of a pump, for example. If the reservoir is arranged in the flow path of the blood or of the plasma, this pump is arranged between the reservoir and the adsorber. A pump arranged in a side branch of the plasma flow or of the blood flow can also be used for emptying the reservoir.

The emptying of the reservoir by one or more metering pumps for regeneration solutions can also take place. Furthermore, the dispensing of the plasma or of the blood can be achieved by mechanically coupled embodiments of the reservoir.

Within the framework of the present invention, a "pump" is understood as any desired conventional pump as well as any other means suitable for conveying fluids.

The pump serving the emptying is preferably arranged between the reservoir and the adsorber. In principle, an arrangement of this pump downstream of the adsorber is also possible and covered by the invention.

Provision can furthermore be made that a pump is arranged in the line and that the reservoir is located between the pump and the adsorber and/or that the reservoir is arranged in the line, in a line branching off from the line or in a line extending in parallel with the line.

It is conceivable that the reservoir is a rigid hollow body or a hollow body having elastic and/or flexible walls.

In the simplest case, it is a rigid, flexible or elastic body having one or more hose connections.

A rigid hollow body can be realized as a hollow part of any desired shape. It preferably has a ventilation and a bleeding device which is e.g. provided with a sterile membrane. The outflow is preferably located at the lowest point.

If it is a flexible hollow body, it can be realized most simply by two films welded to one another in the form of a bag. Other constructions, such as a pair of bellows, can also be realized and are covered by the invention.

An elastic hollow body can be realized by a bag which comprises one or more elastic films, which surrounds the separated plasma or blood and which expands with the received volume. The dispensing of the volume takes place exclusively or supportively due to the elasticity of the bag by the contraction on the opening of the outflow line.

Any desired further technical solutions for reservoirs from combinations of the aforesaid construction principles with fully or partially flexible and/or elastic container walls are also conceivable.

The reservoir can have a ventilation and bleeding device. It is furthermore conceivable that the reservoir has an outflow and an inflow which are formed by separate elements or by one and the same element.

The reservoir can have a volume between 10 ml and 1000 ml.

The reservoir can store the received volume and can also dispense it completely again.

The apparatus preferably has means for controlling or regulating the plasma flow or the blood flow. They are required on the filling and on the emptying of the reservoir since they have a direct effect on the fluid balance of the patient and additionally directly influence the flow over the adsorber. The means are also necessary during the treatment phase in which the blood or plasma is conducted over the adsorber to be able to set a specific flow rate.

An optimization of the processed total flow and of the treatment time can take place by a sensible control or regulation of the additional plasma flow or blood flow from the reservoir. Monitoring means are preferably present which prevent a running empty and an overfilling of the reservoir with the unwanted effects associated therewith. For due to production tolerances of pump hoses, a deviation of the actual conveying rate from the desired conveying rate can be present or differences due to the conveying characteristics of the pumps can occur together with the occurrence of pressure differences.

The apparatus preferably has means for detecting the volume currently stored in the reservoir and for detecting the inflow rate and outflow rate into or out of the reservoir.

A pressure sensor is preferably provided between the plasma separator and the first plasma pump and/or a pressure sensor is provided at the adsorber inlet.

Alternatively or additionally, a pressure sensor can be arranged at the reservoir or before or after the reservoir.

Means are furthermore preferably provided for determining or restricting the quantity of the blood or plasma located in the reservoir. They in particular serve the limitation of the volume stored in the reservoir. This monitoring can take place by the user.

Means are, however, preferably provided which take over this work and which ensure in cooperation with the controller that the quantity does not exceed a maximum value.

The controller is preferably configured such that a completely automated operation of the apparatus takes place. The controller is preferably connected to the means for controlling the fluid flow and preferably operates them autonomously so that an automatic filling and emptying of the reservoir, an automatic application of blood or plasma to the adsorber during the treatment phase and an automatic regeneration of the adsorber take place.

If the reservoir comprises a flexible, but not elastic material, the filling pressure increases considerably on an exceeding of the filling volume. This can be monitored by a pressure restriction in the filling pump or by a separate sensor.

In the case of an elastic or flexible material of the reservoir, the reservoir could be surrounded by a fixed housing for volume restriction. In this case and in the case of a use of a rigid reservoir, a constructional limitation of the maximum volume which can be received in the reservoir results.

It is conceivable that the means are formed by a sensor, in particular by a pressure sensor, by an optical sensor, by an ultrasound sensor, by a position encoder, by a fixed housing for volume limitation, by a balance or by a flow measuring device for measuring the inflow into and the outflow out of the reservoir.

Any other sensors or measuring elements which are suitable for detecting the volume, the mass or the filling level can also be used and are also covered by the invention.

The determination of the volume received in the reservoir by the measurement of inflows and outflows is also covered by the invention. Flow sensors or flow regulators can be used for this purpose.

A mechanical filling level monitoring, e.g. a position encoder for the bag expansion is also conceivable.

The filling volume can also be monitored or measured by technically usual means such as by optical sensors, ultrasound sensors, etc.

The reservoir can also be positioned at a balance independently of the embodiment and of the arrangement in the plasma flow path or in the blood flow path. This has the advantage that only small demands have to be made on the material and on the design of the reservoir and that a precise and direct monitoring of the plasma volume or blood volume in the reservoir is possible by the weighing. At the same time, the inflows and outflows of plasma and blood can be detected at any time and can be used for the process control or process regulation.

In a further embodiment of the invention, a bypass line is provided about the adsorber. The plasma flow or blood flow can be conducted past the adsorber through this line when the reservoir is completely full and the plasma separation or the conveying of the full blood is not to be interrupted. Accordingly, the controller or the switching means can be configured such that it instigates the conveying of the blood or of the plasma through the bypass line when the maximum filling quantity in the reservoir is reached, but the regeneration of the adsorber has not yet ended.

The controller or the switching means can also be configured such that it instigates the suspension of the operation of the blood pump or of the plasma separator when the maximum filling quantity in the reservoir is reached.

In a preferred embodiment of the invention, the technical implementation of the idea in accordance with the invention requires a reservoir for blood or plasma having a sufficient size in the hose system, apparatus for filling and for emptying the reservoir, measures for controlling and monitoring the additional plasma flow in the filling and emptying of the reservoir, apparatus for monitoring the filling level of the reservoir and measures for the safe handling of the apparatus by the user.

The present invention furthermore relates to a method of operating an arrangement having at least one single adsorber for separating substances from blood or from plasma acquired in a plasma separator, wherein blood or plasma is not supplied to the adsorber during the regeneration phase of the adsorber, but is rather buffered in a reservoir, and wherein the buffered blood or plasma is supplied to the adsorber after the regeneration phase of the adsorber.

It is conceivable that the provision of the blood or of the plasma is interrupted when the reservoir has reached a maximum filling level.

Provision is made in a possible embodiment of the invention that the blood or the plasma is conducted past the adsorber in a bypass when the reservoir has reached a maximum filling level. In this case, no interruption of the provision of the blood or of the plasma is provided.

Further preferred features of the method are features of the above-described apparatus for carrying out an apheresis process. In a possible embodiment, the method in accordance with the invention relates to a method of operating an apparatus in accordance with the invention.

Further details and advantages of the invention will be explained in more detail with reference to an embodiment shown in the drawing. There are shown:

FIGS. 1-8: different flowcharts of an apparatus in accordance with the invention.

Elements of the apheresis apparatus in accordance with the invention which are the same or which have the same function are marked by the same reference numerals in the Figures.

FIG. 1 shows a first flowchart of the arrangement in accordance with the invention.

Blood is removed from an arterial inlet A of the patient and is supplied to the plasma separator PS by means of the blood pump P1 which is arranged in the first extracorporeal circuit E1. It can in this respect, for example, be a plasma filter, a centrifuge, etc.

The expression "plasma filter" or "plasma separator" used within the framework of the invention covers any desired device by means of which blood plasma can be taken from the blood of the patient.

The blood components not separated in the plasma separator PS are supplied to the patient again by means of a venous inlet V by the first extracorporeal circuit E1.

The plasma separated in the plasma separator PS is conveyed by the plasma pump P2 through the second extracorporeal circuit E2 into the reservoir PR. The reservoir PR is located in the first line 100. The pump P4 pumps the plasma from the reservoir PR into the adsorber A. As can be seen from FIG. 1, the pump P2 is located upstream of the reservoir PR and the pump P4 is located downstream of the reservoir PR. The plasma purified in the adsorber A moves through the return line 200 back to the extracorporeal circuit E1 with an open valve V1 and is there mixed with the portion of the blood not separated in the plasma separator. This mixture is supplied to the patient via the venous inlet V.

The reference symbol R characterizes a reservoir for a regeneration solution which is conducted for a specific time period over the adsorber A for the regeneration of the adsorber A. The consumed regeneration solution is supplied to a waste container 300 or to another waste receiver with an open valve V2 and a closed valve V1.

The reference symbol K characterizes the connection point of the two extracorporeal circuits E1 and E2.

Figure 2:
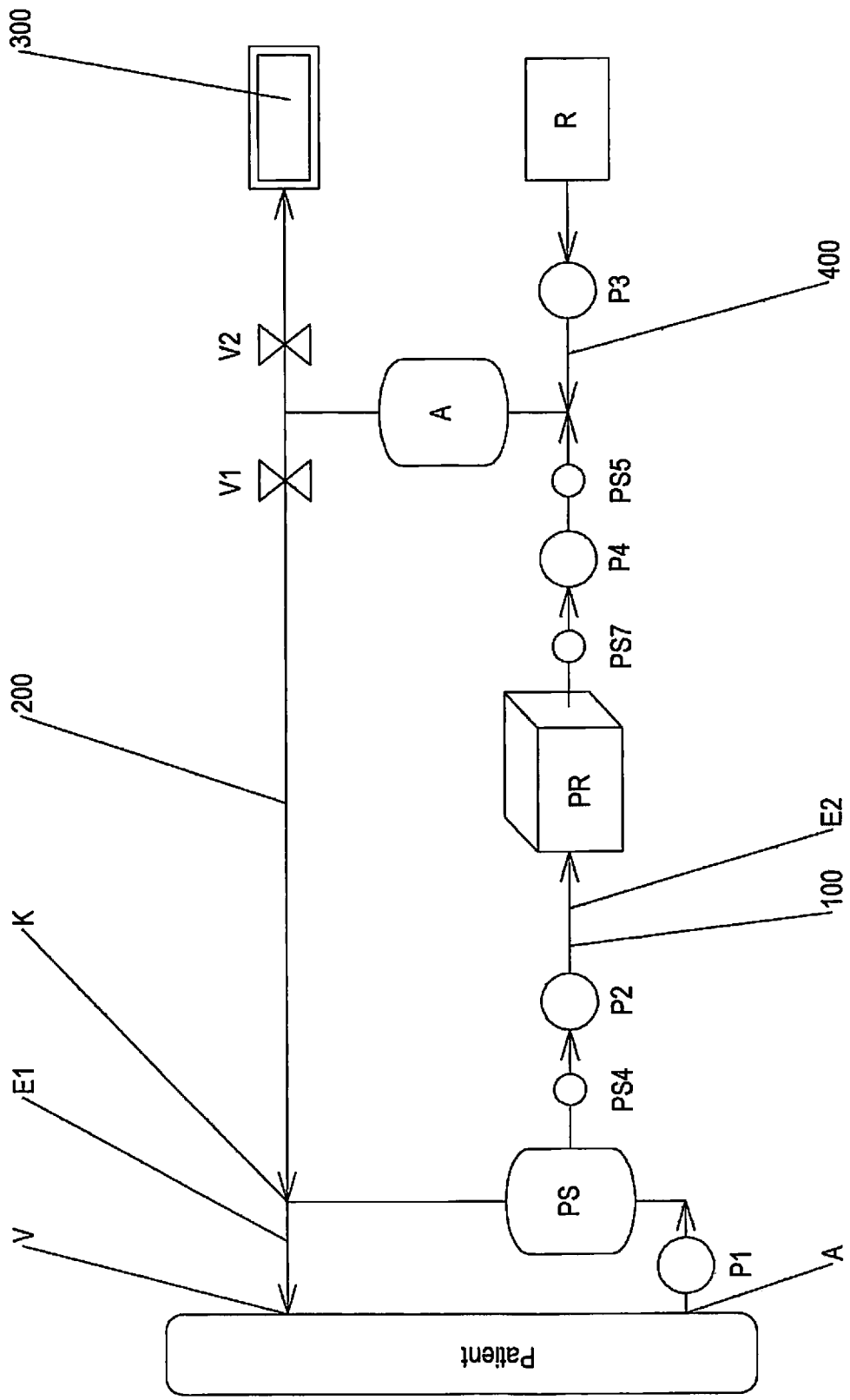
Figure 3:
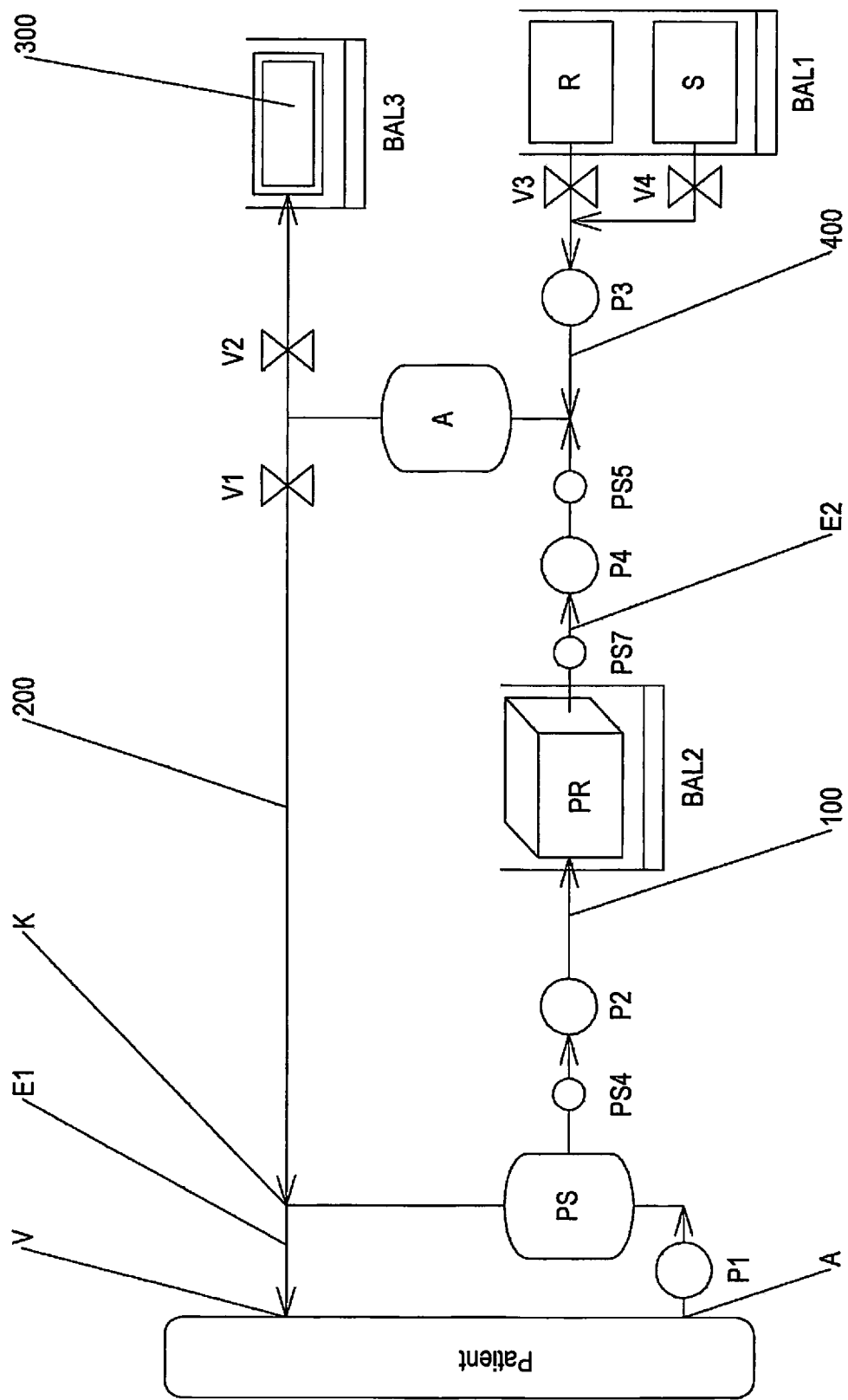

The arrangement in accordance with FIG. 2 differs from the arrangement in accordance with FIG. 1 in that respective pressure sensors PS4, PS7 and PS5 are located between the plasma separator PS and the plasma pump P2, between the reservoir PR and the plasma pump P4 and between the latter and the adsorber A; the function of said pressure sensors will be looked at in more detail within the framework of the explanations with regard to FIG. 3.

As can be seen from FIG. 3, blood is remove from the patient by the pump P1 from an arterial inlet A and an arterial line of the first extracorporeal circuit E1 and is conducted via the plasma separator, e.g. in the form of a plasma filter PS. The second extracorporeal circuit E2, which is connected at the point K to the first extracorporeal circuit E1, extends from the secondary side of the plasma filter PS on which the acquired plasma is present.

The pump P2 which is arranged on the secondary side of the plasma filter PF in the line 100 (in the following also called a "plasma line") generates a vacuum by which a predefined portion of the plasma in the plasma filter PF is separated from the blood of the patient. The pressure sensor PS4 serves the measurement of the vacuum generated by the pump P2.

The plasma separated in the plasma filter PF is likewise conveyed through the pump P2 into the reservoir PR which is likewise located in the plasma line 100. In the embodiment, the reservoir is configured as a film bag having an inflow and an outflow. Reservoirs of any other design can generally also be considered and are covered by the invention.

The capacity of the reservoir lies, for example, at 200 to 1000 ml, preferably at 500 ml. The film bag has no further function beyond the reception of the plasma.

The reservoir PR is arranged on a balance BAL2. It is thereby possible to determine and to monitor the mass or the filling level or the volume of the fluid located in the reservoir PR continuously. The quantity of the plasma or its volume and mass in the reservoir are thus known at all times. This makes it possible to limit by a suitable process control the plasma volume removed as a maximum from the patient, intermittently, i.e. during the regeneration phases of the adsorber A. For this purpose, a maximum value can be stored in the software of the apparatus; the maximum value can be calculated from the patient data by the apparatus or the maximum value can be a combination of the two aforesaid options.

The knowledge of the quantity of the plasma located in the reservoir PR and of the filling level of the reservoir allows an automatic control and optimization of the plasma flow both with respect to the inlet flow into the reservoir and with respect to the outlet flow from the reservoir.

The pressure sensor PS7 which is arranged in the plasma line downstream of the reservoir PR serves to determine a rough malfunction such as the occlusion of the bag outflow or the overfilling of the bag beyond the nominal volume. If the balance BAL2 is reliably configured, the additional pressure sensor PS7 can also be dispensed with.

The pump P4 located downstream of the reservoir PR in the plasma line conveys the plasma out of the reservoir PR and then conducts it over the adsorber A. The pressure sensor PS5 is arranged directly upstream of the adsorber and monitors the inlet pressure of the adsorber. The purified plasma is conducted through the return line 200 back to the extracorporeal circuit E1 via the open valve V1 located downstream of the adsorber and is supplied together with it to the patient.

The line 400 which is in communication, on the one hand, with a reservoir R for regeneration solution for regeneration of the adsorber A and, on the other hand, with a reservoir S for a flushing solution opens into the plasma line 100. Both reservoirs R and S can each be blocked by valves V3 and V4. The conveying of the solutions from the reservoirs R and S takes place by means of the pump P3.

Reference numeral 300 characterizes the receiver for the waste, i.e. for solutions to be discarded.

The operation of the arrangement shown in FIG. 3 is as follows:

Depending on the charge state of the adsorber, a distinction is made between a treatment phase in which the adsorber is charged with substances from the plasma and a regeneration phase in which the charged adsorber is regenerated. The adsorber is charged from the plasma during the treatment phase. The pump P3 is stationary and the valve V2 is closed.

At the start of the treatment, i.e. in a first treatment phase, the pumps P2 and P4, which are located upstream and downstream of the reservoir PR in the line 100, convey at the same flow rate, which has the result that no plasma volume is collected in the reservoir.

If it is found that the receiving capacity of the adsorber A is spent, the regeneration phase of the adsorber A is initiated.

For this purpose, the pump P4 is stopped and the pump P2 continues to run, under certain circumstances at a flow rate reduced with respect to the treatment phase. Since the pump P4 is stationary, the generated plasma is conveyed completely into the reservoir PR. The monitoring of the generated quantity takes place gravimetrically, for example, i.e. by means of the balance BAL2. If the maximum value for the volume located in the reservoir PR is reached, the pump P2 is stopped.

At the end of the regeneration phase, i.e. at the start of the second or following treatment phase, the pump P4 again starts the conveying of the plasma. The pump P2 again conveys at the maximum possible plasma conveying rate, which is in particular the case when the pump P2 was stopped during the regeneration phase or was operated at a reduced flow. The maximum possible conveying rate of the pump P2 results from the blood flow in the extracorporeal circuit E1 and the maximum separable plasma portion.

The conveying rate of the pump P4 is higher than in the first treatment phase. The pump P4 has the object of not only conveying away the plasma conveyed by the pump P2, but additionally also the plasma collected in the reservoir PR in the treatment phase.

If it is found that the reservoir is empty again, for example by a monitoring of the balance BAL2, the flow of the pump P4 is reduced for the remaining residual time of this treatment phase to the flow of the pump P2, which has the consequence that no plasma is collected in the reservoir.

If the adsorber A is completely or largely charged, i.e. if the receiving capacity of the adsorber A is completely or largely spent, the treatment phase is ended and the regeneration phase is initiated.

During the regeneration phase, the pump P4 is stationary and the valve V1 is closed to ensure that no regeneration solution enters into the blood of the patient. Regeneration solution and flushing solution are conveyed through the pump P3 via the adsorber A into the waste container 300 by means of the pump P3 and through valve openings of the valves V3 and V4 in a sequence, flow rate and volume specific to the adsorber A.

As can further be seen from FIG. 3, the reservoir R for regeneration solution and the reservoir S for a flushing solution are arranged on a common balance BAL1. The selection of the solutions (regeneration solution or flushing solution) takes place by means of the valves V3 and V4. The conveying rate of the pump P3 can be compared with the signal of the balance BAL1 and it can be determined in this manner how long or at which conveying rate which solution is conveyed.

To ensure that the correct solution is connected to the correct branch of the hose system, connectors can be used which cannot be confused constructionally. This means that a part of the connector can only be connected to a very specific counter piece.

The same applies accordingly to the insertion or the arming of the hose system with the supply hoses for the regeneration solution and for the flushing solution. It must also be ensured in this respect that they are not inserted swapped over into the valves V3 and V4. This can be ensured, for example, by mechanically different, non-confusably constructed pressure take-off points at the hose system and correspondingly designed receiving points at the device side. A "pressure take-off point" is to be understood as the region of the hose which is inserted into the valve.

It is ensured by this measure and by the unambiguous association of the connector elements that the association of the solution or of the reservoir R and the reservoir S with the valves V3 and V4 is correct.

A further error source is a leak of a valve. A valve V3 or V4 which is not completely closed can thus, for example, have the result that regeneration solution is mixed with the flushing solution or with the fluid flow in an unwanted manner. To ensure that the valves V3 and V4 work correctly, a vacuum can be built up by the pump P3 in the hose segment between the pump P3 and the valves V3 and V4 and the balance BAL1 can be examined for a constant weight before the start of the conveying of the flushing solution, i.e. before the opening of the valve V4. If a weight change is determined, this is due to an incomplete closing of one or both of the valves V3 and V4.

At the same time, a check of the leak tightness, i.e. of the occlusion of the pump P4 and of the valve V1, is carried out on the pressure side of the pump P3. The check for a constant pressure takes place by means of the pressure sensor PS5.

After the successful conclusion of these tests, the valves V2 and V4 are opened and the flushing begins. The conveying of the flushing solution takes place by means of the pump P3.

Alternatively or additionally, valves can be used having a monitoring of the switching state and/or having a monitoring for a correctly inserted hose or valve seat.

As can be seen from FIG. 3, the arrangement has a further balance BAL3 which detects the weight of the waste container 300. A check can be made from a comparison of the weight reduction determined by the balance BAL1 and the weight increase determined by the balance BAL3 whether the valve V1 is closed and the pump P4 is stationary during the flushing and regeneration phase.

A corresponding test can also be carried out for the valves V2, V3 and V4 and for the leak tightness, i.e. occlusion, of the pump P4. With closed valves V1 and V2 and with a stationary pump P3, a pressure is built up by the pump P4 in the line system between P4 and V1, V3 and P3. The pressure can be inspected for constancy by means of the pressure sensor PS5 which is located in this line system. If a constant pressure results, the valve V1 is opened and the treatment phase is started.

An additional examination of the valve V2 during the treatment phase takes place by the measurement of the weight of the waste reservoir 300 by means of the balance BAL3. The pump P3 is monitored for standstill in this phase.

On the transition from plasma to the flushing solution, the flow path from the reservoir S for the flushing solution to the extracorporeal circuit E2 is switched open for a transition time. The valves V4 and V1 are opened and the pump P3 is activated. This process takes so long until the plasma has largely been displaced from the hose system and from the adsorber A by flushing solution.

On the change from flushing solution to plasma, the flow path from the reservoir PR via the valve V2 to the waste 300 is switched free. The conveying of the plasma is carried out in this transition phase for so long until the flushing solution has largely been displaced from the hose system and from the adsorber A by plasma.

In both cases, the security of the process can be ensured by a combination of the aforesaid monitoring processes.

It is ensured by the above-named examinations that the regeneration solution is not diluted by flushing solution and its effectiveness is thus not impaired, the flushing solution is not mixed with regeneration solution and a non-physiologically composed solution is not supplied to the patient in the following treatment, that the regeneration solution and/or the flushing solution is not mixed with plasma in the reservoir and is again supplied to the patient later, that the regeneration solution and/or the flushing solution is not supplied directly to the patient, no unrecognized plasma loss takes place by a valve V2 not sufficiently closed and the regeneration solution and/or flushing solution is not contaminated by plasma.

The statements on the operation of the arrangement in accordance with FIG. 3 apply accordingly to all further embodiments of FIGS. 1, 2 and 4 to 8 where elements are present which are the same or of the same function.

Figure 4:
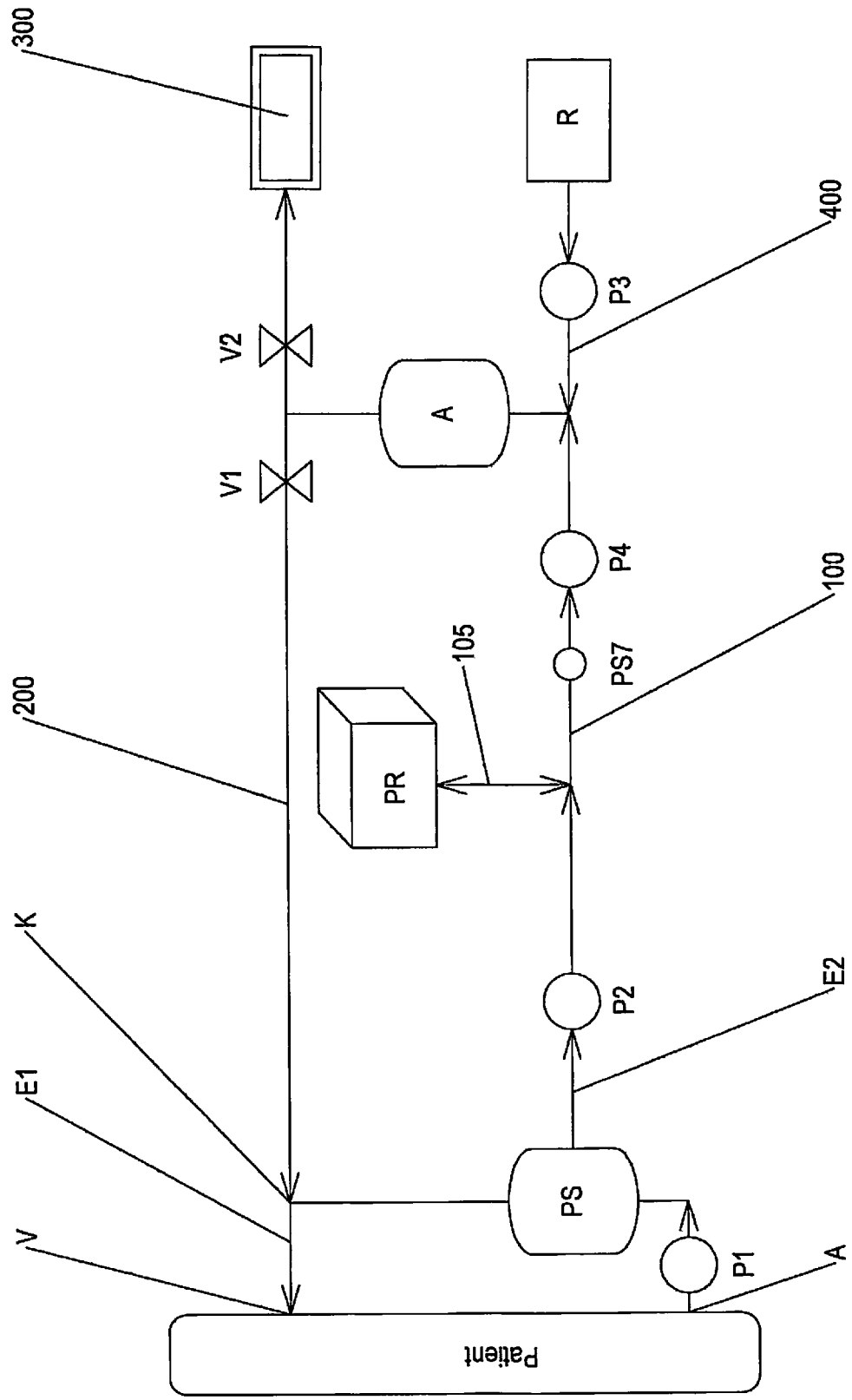

The flowchart in accordance with FIG. 4 corresponds to that of FIG. 1 with the difference that the reservoir PR is not located in the first plasma line 100, but rather in a line 105 branching off therefrom. A further difference from the arrangement in accordance with FIG. 1 comprises the arrangement of a pressure sensor PS7 between the reservoir PR and the plasma pump P4. The pressure sensor PS7 has the object of determining a rough malfunction such as the occlusion of the bag outflow or the overfilling of the bag beyond the nominal volume.

In the arrangements in accordance with FIGS. 1 to 4, the filling of the reservoir PR takes place in each case by means of the pump P2 arranged between the plasma separator PS and the reservoir in the first plasma line 100 and the emptying of the reservoir PR takes place by means of the pump P4 arranged downstream of the reservoir PR in the plasma line 100.

Figure 5:
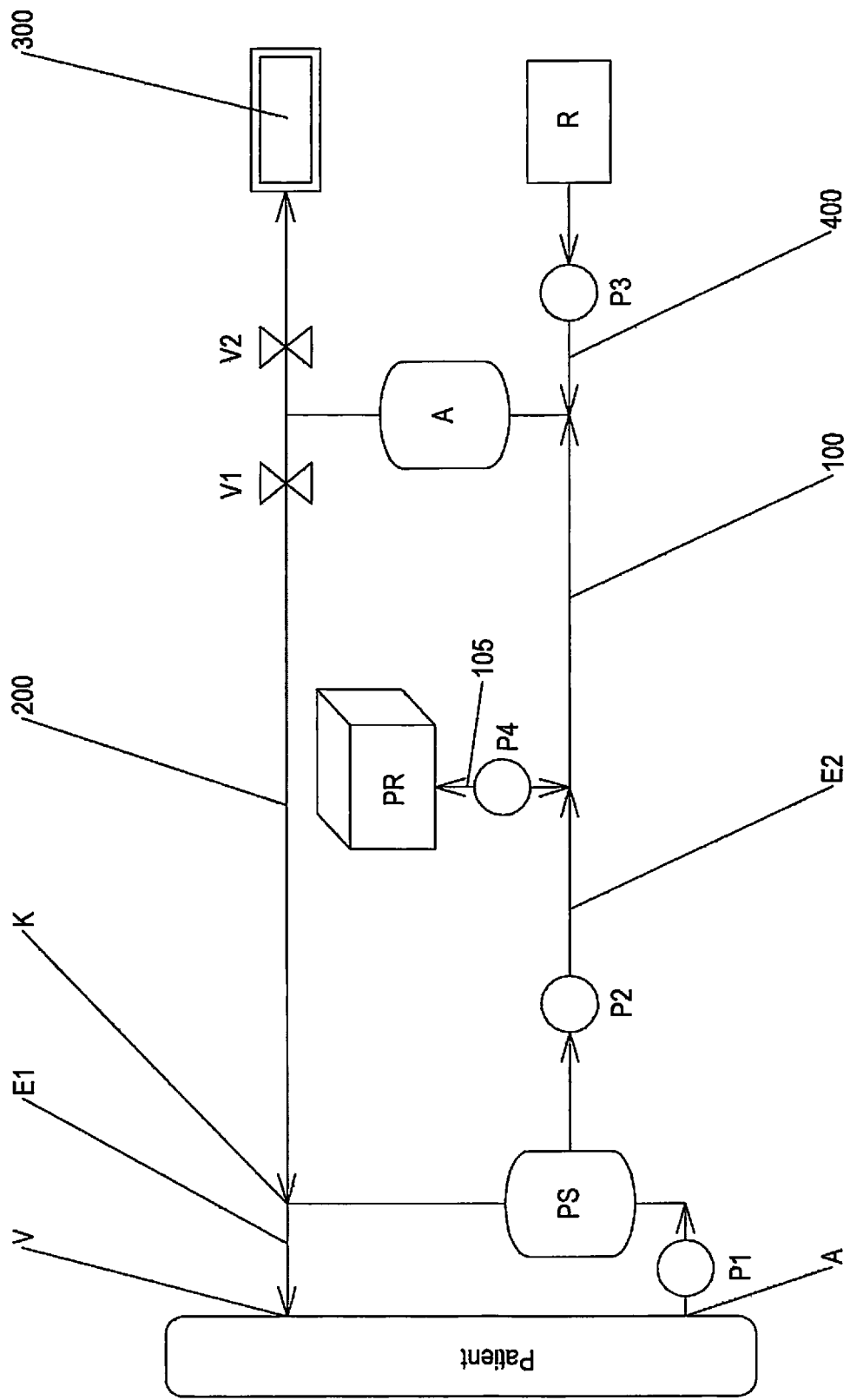

Deviating from this, the reservoir PR and the pup P4 for filling and for emptying the reservoir PR are arranged in the arrangement in accordance with FIG. 5 in a line 105 branching off from the first plasma line 100. The pump P2 conveying the plasma from the plasma filter PF is located between the plasma filter PF and the branch of the line 105 from the first plasma line 100. A single line 105 is provided which serves the filling and emptying of the plasma reservoir PR.

Figure 6:
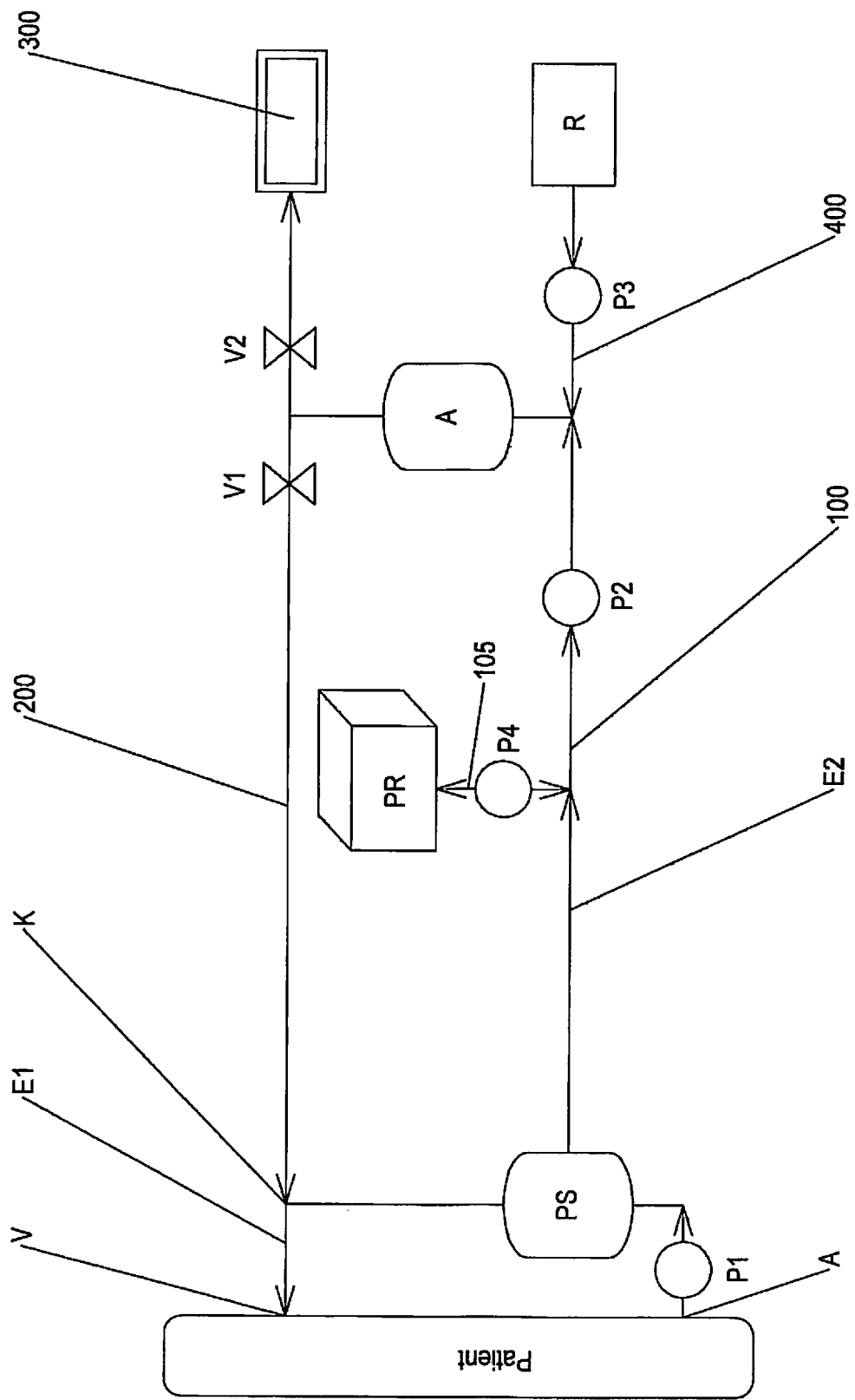

The arrangement in accordance with FIG. 6 corresponds to the arrangement in accordance with FIG. 5 with the difference that the pump P2 is arranged in the first plasma line between the branch of the line 105 from the first plasma line 100 and the adsorber A.

Figure 7:
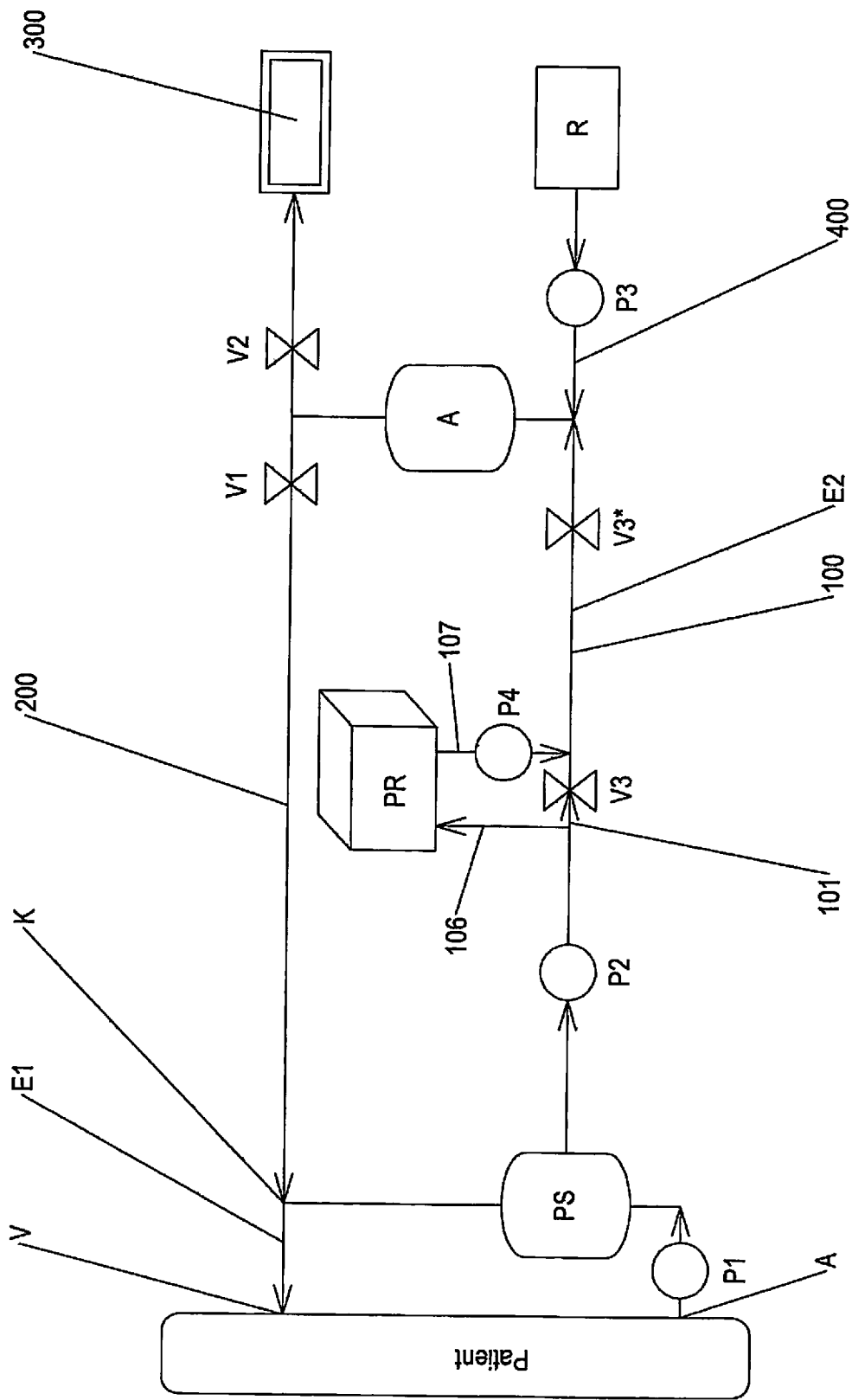

An arrangement can be seen from the flowchart in accordance with FIG. 7 in which the reservoir PR is arranged in lines branching off from the first plasma line 100. These lines are marked by the reference numerals 106, 107.

The line 106 serves the filling of the reservoir PR by means of the pump P2 which is arranged between the plasma filter PF and the branch of the line 106 from the first plasma line 100. The pump P4 is located in the line 107 which opens into the plasma line 100 for emptying the reservoir PR.

The blockable valve V3 is located in the line section 101 of the first plasma line 100 which extends between the two branch points of the lines 106, 107 into or from the first plasma line 100. On the filling of the reservoir PR with plasma, the valve V3 is closed, the pump P2 is running and the pump P4 is stationary. On the emptying of the reservoir PR, the valve V3 is opened and the pumps P2 and P4 are in operation.

The blocking valve V3*, which is likewise arranged in the first plasma line 100 and which is located between the opening points of the lines 106, 107 and the adsorber A, has the object of preventing an entry of regeneration solution into the first plasma line 100 and thus also into the reservoir PR.

Figure 8:
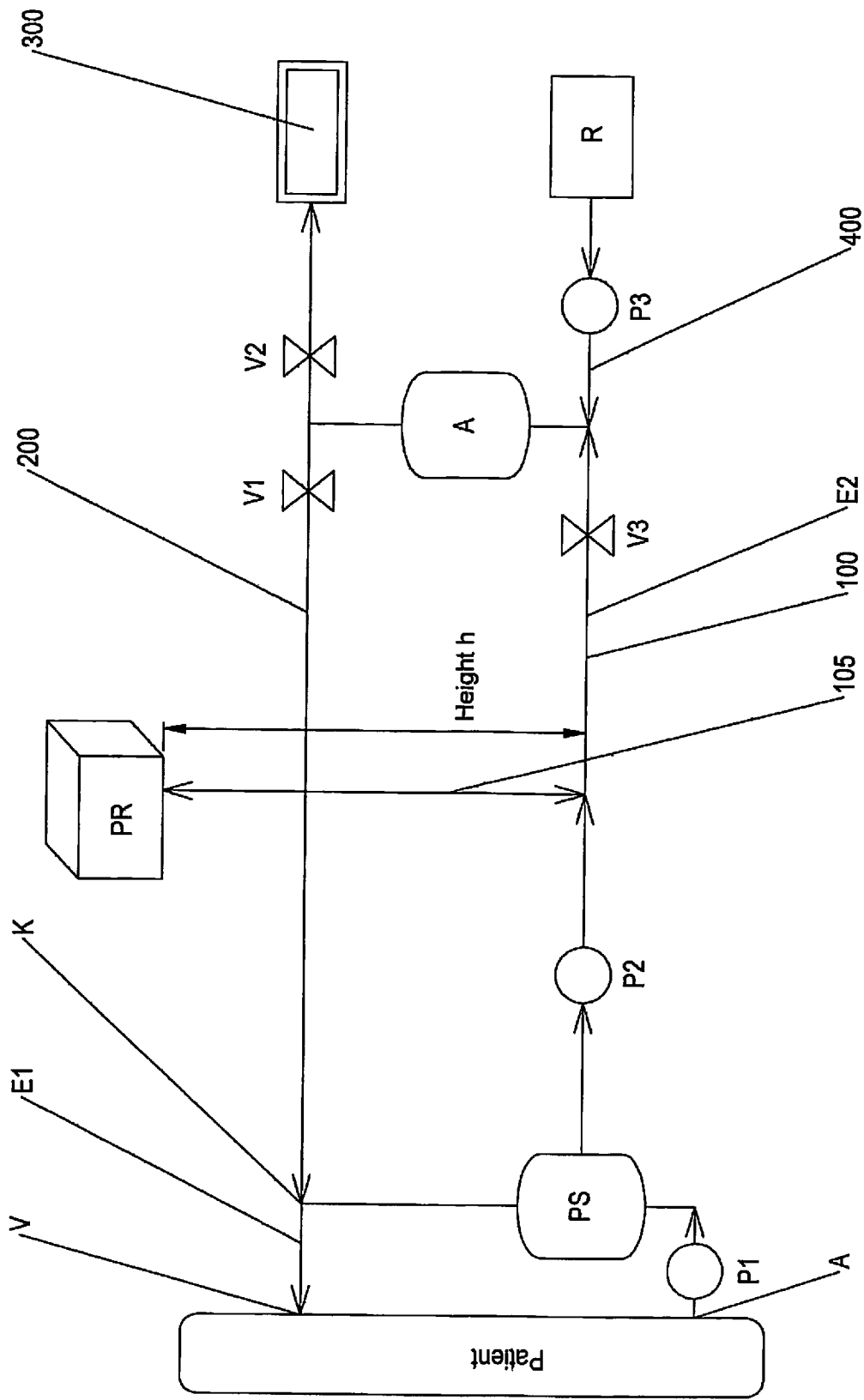

The arrangement in accordance with FIG. 8 is characterized in that the reservoir PR is located in a branch line 105 as is also the case in the arrangement in accordance with FIGS. 4 to 7. Differing from the arrangement in these Figures, no pump is provided for emptying the reservoir PR in accordance with FIG. 8. The filling of the reservoir PR takes place with a closed valve V3 by means of the plasma pump P2 which is arranged between the plasma filter PF and the branch of the line 105 from the first plasma line. The emptying of the reservoir takes place by means of gravity, for which a certain height h is required.

A reservoir R for a regeneration solution is present in the Figures and is connected to the first plasma line 100 via a line 400 in which a pump P3 is located. For the purpose of the regeneration of the adsorber, the line 100 and the return line 200 are closed against the entry of regeneration solution and the valve V2 is opened so that the consumed regeneration solution can enter into the waste 300. Once the regeneration phase is ended, the pump P3 is stopped and the valve V2 is closed.

The invention claimed is:

1. An apparatus for carrying out an apheresis treatment, wherein the apparatus has
    an extracorporeal circuit in which a regenerable single adsorber is located for separating substances from blood or for separating substances from plasma acquired by a plasma separator,
    a line for conducting the blood or the plasma which extends to the adsorber and via which blood or plasma is applied to the adsorber,
    a reservoir for receiving blood or plasma and arranged upstream of the adsorber in the line or in communication with the line upstream of the adsorber,
    a bypass line bypassing the adsorber, and
    a controller or switching means configured such that the reservoir is filled with blood or plasma and the application of blood or plasma to the adsorber is suppressed when the regeneration of the adsorber is carried out, and configured to convey blood or plasma flow through the bypass line when the maximum filing capacity in the reservoir has been reached.

2. An apparatus in accordance with claim 1, characterized in that a first extracorporeal circuit is provided in which the plasma separator is located whose secondary side is adjoined by a second extracorporeal circuit, wherein the reservoir and the adsorber are arranged in the second extracorporeal circuit, and wherein a return line is provided which connects the adsorber to the first extracorporeal circuit at the outlet side.

3. An apparatus in accordance with claim 1, characterized in that means are provided, preferably in the form of pumps and/or valves, for emptying the reservoir; and in that the controller or switching means are in communication with the means for emptying the reservoir such that they can be actuated by the controller or by the switching means when the regeneration phase of the adsorber has ended.

4. An apparatus in accordance with claim 1, characterized in that means for filling the reservoir are formed by a pump arranged downstream of the plasma separator, by the blood pump, by a pump which is arranged in a line leading to the reservoir or by a pneumatic actuator.

5. An apparatus in accordance with claim 3, characterized in that the means for emptying the reservoir are formed by gravity, by a pump arranged downstream of the reservoir, by a pump which is arranged in a line leading off from the reservoir, by a pneumatic actuator or by the elastic material of the reservoir.

6. An apparatus in accordance with claim 1, characterized in that a pump is arranged in the line and that the reservoir is located between the pump and the adsorber and/or that the reservoir is arranged in the line, in a line branching off from the line or in a line extending in parallel with the line.

7. An apparatus in accordance with claim 1, characterized in that the reservoir is a rigid hollow body or a hollow body having elastic and/or flexible walls, with provision preferably being made that the reservoir has a ventilation and bleeding device; and/or in that the reservoir has an outflow and an inflow which are formed by separate elements or by one and the same element; and/or characterized in that the reservoir has a volume between 10 ml and 1000 ml.

8. An apparatus in accordance with claim 1, characterized in that means are provided for determining and/or monitoring and/or limiting the quantity of the blood or plasma located in the reservoir.

9. An apparatus in accordance with claim 8, characterized in that the means are formed by a sensor, in particular by a pressure sensor, by an optical sensor, by an ultrasound sensor, by a position encoder, by a fixed housing for volume limitation, by a set of scales or by a flow measuring device for measuring the inflow into and the outflow out of the reservoir.

10. An apparatus in accordance with claim 1, characterized in that the controller or the switching means is configured such that the suspension of the operation of the blood pump or of the plasma separator can be effected by them when the maximum filling quantity in the reservoir has been reached.

11. A method of operating an arrangement having a regenerable single adsorber for separating substances from blood or for separating substances from a plasma acquired in a plasma separator, characterized in that blood or plasma is not supplied to the adsorber during the regeneration phase of the adsorber, but is rather buffered in a reservoir; in that the blood or the plasma is conveyed in a bypass line bypassing the adsorber when the reservoir has reached a maximum filling level; and in that the buffered blood or plasma is supplied to the adsorber after the regeneration phase of the adsorber.

12. A method in accordance with claim 11, characterized in that the provision of the blood or of the plasma is interrupted when the reservoir has reached a maximum filling level.

* * * * *